US010065831B2

(12) United States Patent
Wiedmann et al.

(10) Patent No.: US 10,065,831 B2
(45) Date of Patent: Sep. 4, 2018

(54) METHODS AND APPARATUSES FOR FOLDING ABSORBENT ARTICLES

(71) Applicant: The Procter & Gamble Company, Cincinnati, OH (US)

(72) Inventors: Peter Wiedmann, Montgomery, OH (US); Todd Douglas Lenser, Liberty Township, OH (US); Ricky Reynaldo Yanez, Jr., Cincinnati, OH (US); Yoichiro Yamamoto, Cologne (DE); Andreas Josef Dreher, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 734 days.

(21) Appl. No.: 14/273,813

(22) Filed: May 9, 2014

(65) Prior Publication Data
US 2014/0342894 A1 Nov. 20, 2014

Related U.S. Application Data

(60) Provisional application No. 61/824,003, filed on May 16, 2013.

(51) Int. Cl.
*B65H 45/28* (2006.01)
*B65H 45/16* (2006.01)
(Continued)

(52) U.S. Cl.
CPC ....... *B65H 45/28* (2013.01); *A61F 13/15747* (2013.01); *B65H 45/16* (2013.01);
(Continued)

(58) Field of Classification Search
CPC ...... B65H 45/16; B65H 45/161; B65H 45/18; B65H 45/28; B65H 2801/57; B65H 29/12;
(Continued)

(56) References Cited

U.S. PATENT DOCUMENTS 3,339,914 A 9/1967 Grantham
3,692,303 A 9/1972 Grantham
(Continued)

FOREIGN PATENT DOCUMENTS

GB 1 253 503 A 11/1971
JP H10-7317 1/1989
(Continued)

OTHER PUBLICATIONS

PCT International Search Report, dated Jul. 16, 2014, 8 pages.
(Continued)

*Primary Examiner* — Hemant M Desai
*Assistant Examiner* — Eduardo R Ferrero
(74) *Attorney, Agent, or Firm* — Charles R. Matson

(57) ABSTRACT

The present disclosure relates to methods and apparatuses for manufacturing absorbent articles. More particularly, the systems and methods for folding absorbent articles advancing in a converting line may be configured with tucker blades that prevent opposing end regions of absorbent articles from colliding directly with each other as the absorbent articles are being folded.

18 Claims, 12 Drawing Sheets

(51) Int. Cl.
*B65H 45/18* (2006.01)
*A61F 13/15* (2006.01)

(52) U.S. Cl.
CPC ........ *B65H 45/18* (2013.01); *A61F 13/15585* (2013.01); *B65H 45/164* (2013.01); *B65H 2701/19* (2013.01); *B65H 2701/1924* (2013.01); *B65H 2801/57* (2013.01)

(58) Field of Classification Search
CPC ........ B65H 29/58; B65H 29/60; B65H 29/62; B65H 45/04; B65H 45/10; B65H 45/1015; B65H 47/34; B65H 47/52; B65H 47/82; B65H 47/252; B65H 45/164; B65H 2701/19; B65H 2701/1924; A61F 13/15747; A61F 13/15585; B65G 47/52; B65G 47/82
See application file for complete search history.

(56) References Cited

U.S. PATENT DOCUMENTS

| | | |
|---|---|---|
| 4,053,150 A | 10/1977 | Lane |
| 4,122,939 A * | 10/1978 | Langen ................ B65B 35/24 198/476.1 |
| 4,519,596 A | 5/1985 | Johnson et al. |
| 4,650,173 A | 3/1987 | Johnson et al. |
| 4,715,846 A | 12/1987 | Zak |
| 4,738,440 A | 4/1988 | Weir |
| 5,358,464 A | 10/1994 | Funk et al. |
| 5,980,439 A | 11/1999 | Johnson et al. |
| 6,132,532 A | 10/2000 | Shepelev et al. |
| 6,450,321 B1 | 9/2002 | Blumenthal et al. |
| 6,705,453 B2 | 3/2004 | Blumenthal et al. |
| 6,708,855 B2 | 3/2004 | Wilson et al. |
| 6,811,019 B2 | 11/2004 | Christian et al. |
| 6,814,217 B2 | 11/2004 | Blumenthal et al. |
| 6,915,929 B2 | 7/2005 | Rauch et al. |
| 7,617,656 B2 | 11/2009 | Weidmann |
| 8,002,256 B2 | 8/2011 | Sasahara |
| 8,145,338 B2 | 3/2012 | Kent et al. |
| 2001/0038709 A1 | 11/2001 | Bett et al. |
| 2003/0062121 A1 | 4/2003 | Franklin et al. |
| 2003/0110739 A1 | 6/2003 | Saas |
| 2005/0233881 A1 | 10/2005 | Meyer |
| 2006/0254881 A1* | 11/2006 | Furthmueller ......... B65G 15/58 198/419.2 |
| 2007/0142798 A1 | 6/2007 | Goodlander et al. |
| 2007/0142806 A1 | 6/2007 | Roe et al. |
| 2007/0287983 A1 | 12/2007 | Lodge et al. |
| 2008/0132865 A1 | 6/2008 | Li et al. |
| 2008/0223537 A1 | 9/2008 | Wiedmann |
| 2009/0026687 A1 | 1/2009 | Sasahara |
| 2010/0012285 A1 | 1/2010 | Wiedmann et al. |
| 2010/0305738 A1 | 12/2010 | Debruler et al. |
| 2010/0305740 A1 | 12/2010 | Kent et al. |
| 2011/0003673 A1 | 1/2011 | Piantoni et al. |
| 2011/0247199 A1 | 10/2011 | LaVon et al. |
| 2012/0247661 A1 | 10/2012 | Ogasawara et al. |
| 2013/0001042 A1 | 1/2013 | Yamamoto |
| 2013/0062263 A1 | 3/2013 | Nakano |
| 2013/0180835 A1* | 7/2013 | Ishikawa ........... A61F 13/15764 198/890 |
| 2015/0374555 A1* | 12/2015 | Chen ................. A61F 13/15747 493/427 |

FOREIGN PATENT DOCUMENTS

| | | |
|---|---|---|
| JP | S64-69465 | 3/1989 |
| JP | 2002-079187 | 3/2002 |
| JP | 2010-207457 | 9/2010 |
| WO | WO 2012/043865 A1 | 4/2012 |

OTHER PUBLICATIONS

U.S. Appl. No. 61/823,992, filed May 16, 2013, Wiedmann, et al.
U.S. Appl. No. 61/824,013, filed May 16, 2013, Wiedmann, et al.
All Office Actions, U.S. Appl. No. 14/273,836.
All Office Actions, U.S. Appl. No. 14/273,671.

* cited by examiner

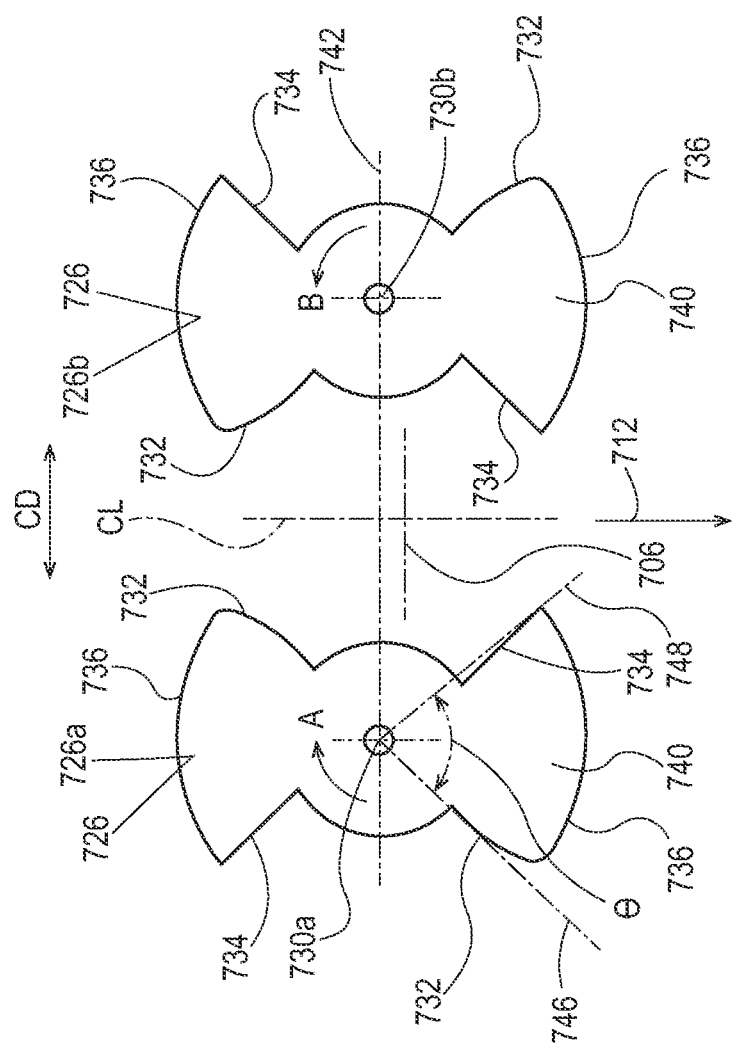

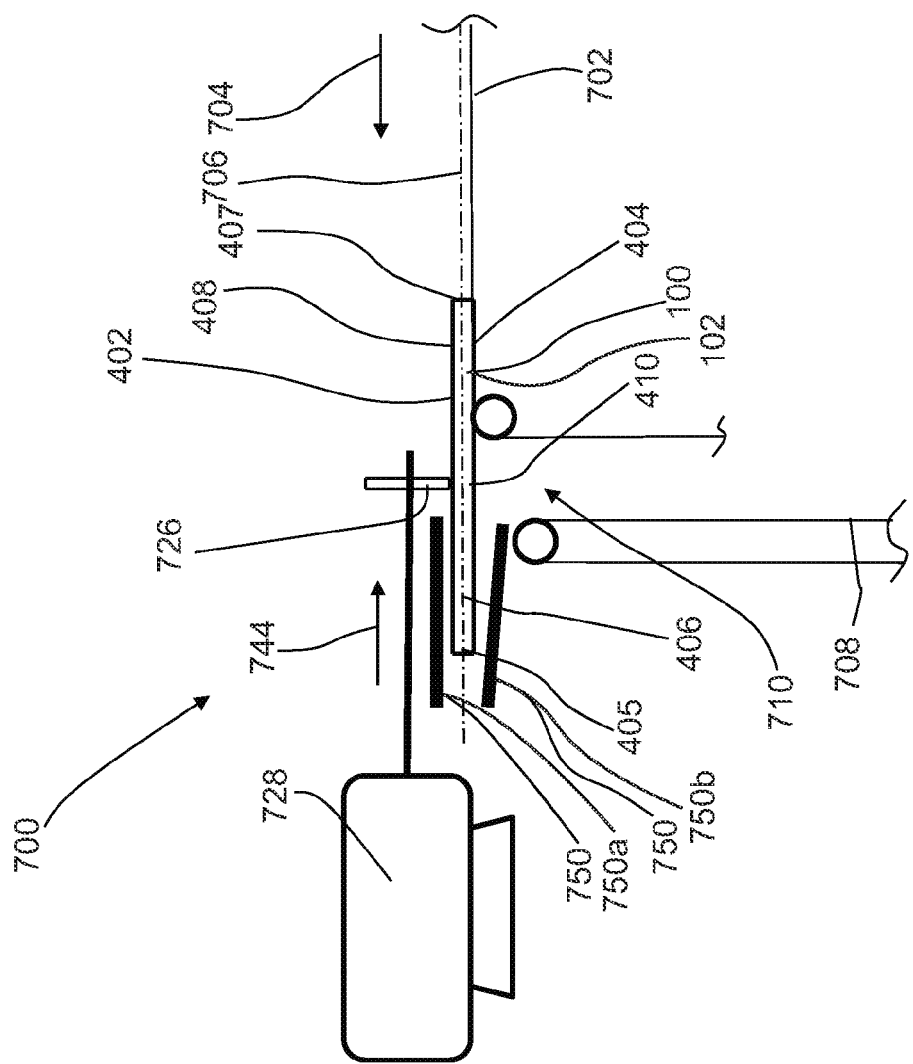

METHODS AND APPARATUSES FOR FOLDING ABSORBENT ARTICLES

CROSS REFERENCE TO RELATED APPLICATION

This application claims the benefit of U.S. Provisional Application No. 61/824,003, filed on May 16, 2013, which is hereby incorporated by reference.

FIELD OF THE INVENTION

The present disclosure relates to systems and methods for folding disposable absorbent articles, and more particularly, apparatuses and methods utilizing tucker blades that prevent opposing end regions of absorbent articles from colliding with each other during the folding process.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles.

After the final knife cut, the discrete diapers or absorbent articles may also then be folded prior to being packaged. For example, some process may be configured to fold absorbent articles into a U-shape about a lateral centerline, wherein folding blades engage and force advancing absorbent articles into a nip between two conveyor belts. In an effort to save on capital expenses, absorbent article manufacturers are often looking for ways produce more articles in shorter periods of time by increasing production line speeds. As production line speeds increase, the machine direction speeds at which assembled absorbent articles travel increase. In turn, the speeds at which absorbent articles are folded also increase.

Existing systems for folding absorbent articles may have some disadvantages that become accentuated as a result of the increased article travel speeds. In some instances, the absorbent articles may include various types of components that may become damaged and/or displaced during the folding process when conducted at relative high speeds. For example, some taped diapers may include front and back ears or connecting tabs that are connected with opposing front and rear waist regions of the diapers. During the manufacturing process, it may be desirable to have the front and back ears turned laterally inward and onto the topsheet before the diaper is folded. During the diaper folding process, folding blades may contact the crotch region of the diaper, forcing the diaper into a folding nip. Subsequently, the front and rear waist regions may collide with each other as the crotch region of the diaper is forced into the nip. At relatively high speeds, the collision of the front and rear waist regions during the folding process may damage or displace the front and/or back ears.

Consequently, it would be beneficial to provide a system for reliable, high speed folding of absorbent articles that is configured to help avoid damage to and/or unintended displacement of article components. In addition, a system that utilizes some or all existing equipment and/or control mechanisms to fold products rather than a complete replacement system to perform folding operations may be desirable.

SUMMARY OF THE INVENTION

The present disclosure relates systems and methods for folding absorbent articles with tucker blades that prevent opposing end regions of absorbent articles from colliding directly with each other as the absorbent articles are being folded.

In one form, a method for folding absorbent articles includes the steps of: conveying an absorbent article in a first direction on a first carrier to define an article transport plane, wherein the absorbent article includes a first surface and a second surface opposite the first surface, wherein the absorbent article includes a first end and a second end, and wherein the absorbent article includes a first end region and a second end region, and a central region located between the first and second end regions; advancing the first end and the first end region past a nip defined between the first carrier and a second carrier; rotating a tucker blade, wherein the tucker blade includes a first surface and a second surface opposite the first surface, and wherein the tucker blade includes a leading edge and a trailing edge, wherein the leading edge and the trailing edge move through the article transport plane at the nip as the tucker blade rotates; folding the absorbent article by redirecting the central region of the absorbent article in a second direction into the nip with the leading edge of the tucker blade thereby creating a fold line across the central region of the absorbent article, positioning the first surface of the first end region of the absorbent article into a facing relationship with the first surface of the tucker blade and positioning the first surface of the second end region of the absorbent article into a facing relationship with the second surface of the tucker blade, wherein the first end and the second end of the absorbent article are separated by the tucker blade; and conveying the folded absorbent article in the second direction between the first carrier and the second carrier away from the article transport plane.

In another form, a method for folding absorbent articles includes the steps of: advancing a continuous length of absorbent articles at a first speed, S1, in a machine direction; cutting the continuous length of absorbent articles into discrete absorbent articles, wherein each discrete absorbent article includes a first surface and a second surface opposite the first surface, wherein each discrete absorbent article includes a first end region and a second end region, and a central region located between the first and second end regions, and wherein each discrete absorbent article includes a first end and a second end, and a having a pitch length, PL, defined by a distance in the machine direction between the first end and the second end; conveying each discrete absorbent articles at a second speed, S2, in a first direction on a first carrier to define an article transport plane; advancing the first end and the first end region of each discrete absorbent article past a nip defined between the first carrier and a second carrier; rotating a tucker blade, wherein the tucker blade includes a first surface and a second surface opposite the first surface, and wherein the tucker blade includes a leading edge and a trailing edge, wherein the leading edge and the trailing edge move through the article transport plane at the nip as the tucker blade rotates; folding n discrete absorbent articles with one full revolution of the tucker blade by redirecting the central region of each discrete absorbent article in a second direction into the nip with the leading edge thereby creating a fold line across the central region of each discrete absorbent article, positioning the first surface of the first end region into a facing relationship with the first surface of the tucker blade and positioning the first surface of the second end region into a facing relationship with the second surface of the tucker blade, and wherein a sweep angle, θ, between the leading edge and the trailing edge of the tucker blade is calculated as $(0.18*PL*S1)/(S2*n)$.

In yet another form, an apparatus for folding absorbent articles includes: a knife adapted to cut discrete absorbent articles from a continuous length of absorbent articles advancing in a machine direction at a first speed, S1, and wherein each discrete absorbent article defines a pitch length, PL; a first carrier adapted to convey an absorbent article in a first direction and a second direction at a second speed, S2; a second carrier adjacent the first carrier to define a nip extending in the second direction; a tucker blade including a first surface and a second surface opposite the first surface, and wherein the tucker blade includes a leading edge and a trailing edge, wherein the leading edge and the trailing edge move through the article transport plane at the nip as the tucker blade rotates; and a motor adapted to rotate the tucker blade so as to redirect n discrete absorbent articles into the nip with one full revolution; and wherein a sweep angle, θ, between the leading edge and the trailing edge of the tucker blade is calculated as $(0.18*PL*S1)/(S2*n)$.

BRIEF DESCRIPTION OF THE DRAWINGS

FIG. 3A is a view of two tucker blades from FIG. 3 taken along line 3A-3A.

FIG. 9 is a detailed view of an embodiment of a folding system including guide plates.

DETAILED DESCRIPTION OF THE INVENTION

Figure 1:
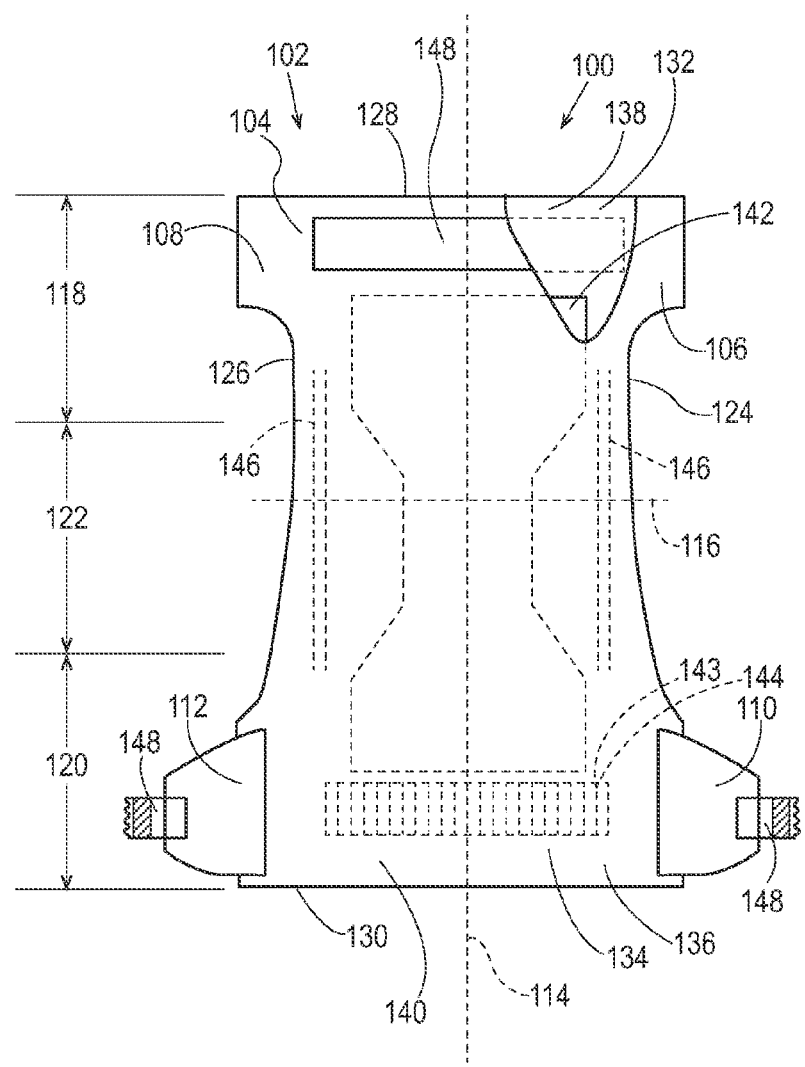
FIG. 1 is a top plan view of a disposable absorbent article that may include one or more substrates and/or components constructed and folded in accordance with the present disclosure.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from an end edge, such as a waist edge to a longitudinally opposing end edge, or waist edge, of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a defined woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The present disclosure relates to methods and apparatuses for manufacturing absorbent articles, and more particularly, systems and methods for folding absorbent articles advancing in a converting line. As discussed in more detail below, the folding processes and apparatuses herein may be configured with tucker blades that prevent opposing end regions of absorbent articles from colliding directly with each other as the absorbent articles are being folded. During the converting process, various continuous substrates and/or discrete components may be combined with each other to form a continuous length of absorbent articles. At a downstream portion of the converting process, the continuous length of absorbent articles may be subjected to a final knife and cut to create separate and discrete absorbent articles in the form of diapers. Each discrete absorbent article includes a first surface and a second surface opposite the first surface, and each discrete absorbent article includes a first end and a second end, as well as a first end region and a second end region separated from each other by a central region. From the final knife, the discrete absorbent articles may then advance to a folding system. More particularly, the folding system includes a first carrier that advances the absorbent articles in a first direction to define an article transport plane. A second carrier is located adjacent the first carrier to define a nip extending in a second direction, and one or more tucker blades are rotated adjacent the nip. As discussed in more detail, each tucker blade includes a leading edge and a trailing edge that move through the article transport plane as the tucker blade rotates. The first carrier then advances the first end and the first end region of each discrete absorbent article past the nip. The discrete absorbent articles are then folded by redirecting the central region of each absorbent article in a second direction into the nip with the leading edge of the tucker blade, thereby creating a fold line across the central region of the absorbent article.

As discussed in more detail below, the tucker blades each include a first surface and a second surface opposite the first surface. The tucker blades are configured such that as the leading edge continues to push the article along the fold line in the second direction through the nip, the first surface of the first end region of the absorbent article is brought into a facing relationship with the first surface of the tucker blade. At the same time, the first surface of the second end region of the absorbent article is brought into a facing relationship with the second surface of the tucker blade. And the first end and the second end of the folded absorbent article are separated by tucker blade. As such, the first and the second end regions of the absorbent articles do not collide with each other during the folding process. Instead, the first and second end regions of the absorbent article are brought into contact with opposing sides of the tucker blade. From the tucker blade, the folded absorbent articles are conveyed in the second direction between the first carrier and the second carrier away from the article transport plane.

It is to be appreciated that although the methods and apparatuses herein may be configured to fold various types of products, the methods and apparatuses herein are discussed below in the context of manufacturing absorbent articles. In particular, the methods and apparatuses are discussed in the context of folding advancing diapers during production. For the purposes of a specific illustration, FIG. 1 shows one example of a disposable absorbent article 100, such as described in U.S. Patent Publication Nos. US2008/0132865 A1 and US2011/0247199 A1, in the form of a diaper 102 that may be constructed from substrates and components monitored according to the systems and methods disclosed herein. In particular, FIG. 1 is a plan view of one embodiment of a diaper 102 including a chassis 104 shown in a flat, unfolded condition, with the portion of the diaper 102 that faces away from the wearer oriented towards the viewer. A portion of the chassis structure is cut-away in FIG. 1 to more clearly show the construction of and various features that may be included in embodiments of the diaper.

As shown in FIG. 1, the diaper 102 includes a chassis 104 having a first ear 106, a second ear 108, a third ear 110, and a fourth ear 112. To provide a frame of reference for the present discussion, the chassis 104 is shown with a longitudinal axis 114 and a lateral axis 116. The chassis 104 is shown as having a first waist region 118, a second waist region 120, and a crotch region 122 disposed intermediate the first and second waist regions. In some configurations, the first waist region 118 may correspond with a front waist region, and the second waist region 120 may correspond with a rear waist region. The periphery of the diaper is defined by a pair of longitudinally extending side edges 124, 126; a first outer edge 128 extending laterally adjacent the first waist region 118; and a second outer edge 130 extending laterally adjacent the second waist region 120. As shown in FIG. 1, the chassis 104 includes an inner, body-facing surface 132, and an outer, garment-facing surface 134. A portion of the chassis structure is cut-away in FIG. 1 to more clearly show the construction of and various features that may be included in the diaper. As shown in FIG. 1, the chassis 104 of the diaper 102 may include an outer covering layer 136 including a topsheet 138 and a backsheet 140. An absorbent core 142 may be disposed between a portion of the topsheet 138 and the backsheet 140. As discussed in more detail below, any one or more of the regions may be stretchable and may include an elastomeric material or laminate as described herein. As such, the diaper 102 may be configured to adapt to a specific wearer's anatomy upon application and to maintain coordination with the wearer's anatomy during wear.

The absorbent article may also include an elastic waist feature 143 shown in FIG. 1 in the form of a waist band 144 and may provide improved fit and waste containment. The elastic waist feature 143 may be configured to elastically expand and contract to dynamically fit the wearer's waist. The elastic waist feature 143 can be incorporated into the diaper and may extend at least longitudinally outwardly from the absorbent core 142 and generally form at least a portion of the first and/or second outer edges 128, 130 of the diaper 102. In addition, the elastic waist feature may extend laterally to include the ears. While the elastic waist feature 143 or any constituent elements thereof may comprise one or more separate elements affixed to the diaper, the elastic waist feature may be constructed as an extension of other elements of the diaper, such as the backsheet 140, the topsheet 138, or both the backsheet and the topsheet. In addition, the elastic waist feature 143 may be disposed on the outer, garment-facing surface 134 of the chassis 104; the inner, body-facing surface 132; or between the inner and outer facing surfaces. The elastic waist feature 143 may be constructed in a number of different configurations including those described in U.S. Patent Publication Nos. US2007/0142806A1; US2007/0142798A1; and US2007/0287983A1, all of which are hereby incorporated by reference herein.

As shown in FIG. 1, the diaper 102 may include leg cuffs 146 that may provide improved containment of liquids and other body exudates. In particular, elastic gasketing leg cuffs can provide a sealing effect around the wearer's thighs to prevent leakage. It is to be appreciated that when the diaper is worn, the leg cuffs may be placed in contact with the wearer's thighs, and the extent of that contact and contact pressure may be determined in part by the orientation of diaper on the body of the wearer. The leg cuffs 146 may be disposed in various ways on the diaper 102.

The diaper 102 may be provided in the form of a pant-type diaper or may alternatively be provided with a re-closable fastening system, which may include fastener elements in various locations to help secure the diaper in position on the wearer. For example, fastener elements 148 may be located on the first and second ears 110, 112 and may be adapted to releasably connect with one or more corresponding fastening elements located in the first or second waist regions. It is to be appreciated that various types of fastening elements may be used with the diaper.

Figure 2:
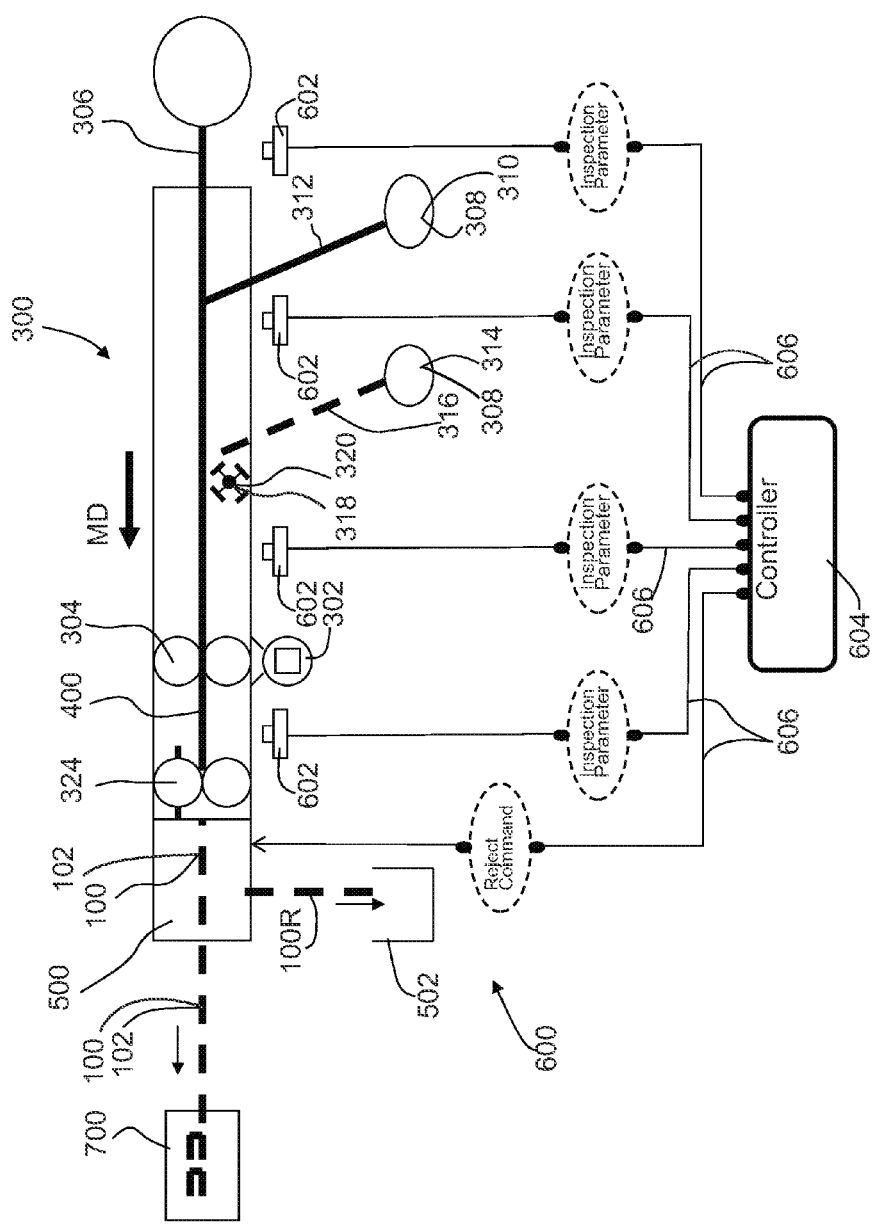
FIG. 2 is a schematic representation of an absorbent article converting line and folding system.

FIG. 2 shows a schematic representation of an absorbent article converting process including a converting line or machine 300 configured to manufacture absorbent articles 100. It is to be appreciated that the systems and methods disclosed herein are applicable to work with various types of converting processes and/or machines. As shown in FIG. 2, the converting line 300 may include one or more motors 302 that drive transport systems, such as a nip roll 304, to move diaper substrates and component materials through the manufacturing process. For example, FIG. 2 shows a base substrate 306 and two auxiliary substrates and/or components 308 of material used to construct portions of the diapers. The substrates may be provided as rolls and fed into the converting line 300. It is to be appreciated that material of the auxiliary substrates may be supplied in various ways. For example, FIG. 2 shows a first auxiliary substrate 310 in the form of a continuous substrate 312, and a second auxiliary substrate 314 in the form of individual components 316. It is to be appreciated that the auxiliary substrates 310 may be transferred to the base substrate through various types of transfer mechanisms. For example, the individual components 316 are shown as being transferred to the base substrate via a transfer mechanism 318 in the form of a servo patch placer mechanism 320, such as disclosed in U.S. Pat. Nos. 6,450,321; 6,705,453; 6,811,019; and 6,814,217. It is also to be appreciated that the various substrates can be used to construct various components of the absorbent articles, such as backsheets, topsheets, ears, leg cuffs, elastic waist features, and absorbent cores. Exemplary descriptions of absorbent article components are provided above with reference to FIG. 1.

Referring back to FIG. 2, as the base substrate 306 advances through the converting line 300, the base substrate 306 is combined with the auxiliary substrates 308 and/or discrete components 316 to create a continuous length of absorbent articles 400. At a downstream portion of the converting process 300, the continuous length of absorbent articles 400 is subjected to a final knife 324 and cut to create separate and discrete absorbent articles 100 in the form of diapers 102. An inspection system 600 may identify the defective absorbent articles 100R. In turn, defective articles 100R may be subject to a rejection system 500 and removed from the process. For example, FIG. 2 shows defective articles 100R being channeled to a reject bin 502. It is to be appreciated that various types of inspection system 600 configurations may be utilized, such as for example disclosed in U.S. Pat. No. 8,145,338, and may include various types of sensors 602 connected with a controller 604 over a communication network 606. Articles 100 that are not deemed to be defective may be subject to further processing steps, such as folding and packaging. For example, FIG. 2 shows diapers 102 advancing from the final knife 324 to a folding system 700.

It is to be appreciated that the term "reject bin" is used herein generically to designate the location where rejected diapers may be conveyed. As such, the reject bin 502 may include various systems. For example, the reject bin may 502 may include additional systems such as conveyors and/or pneumatic systems to provide additional transport or conveyance of rejected diapers to other locations.

Figure 3:
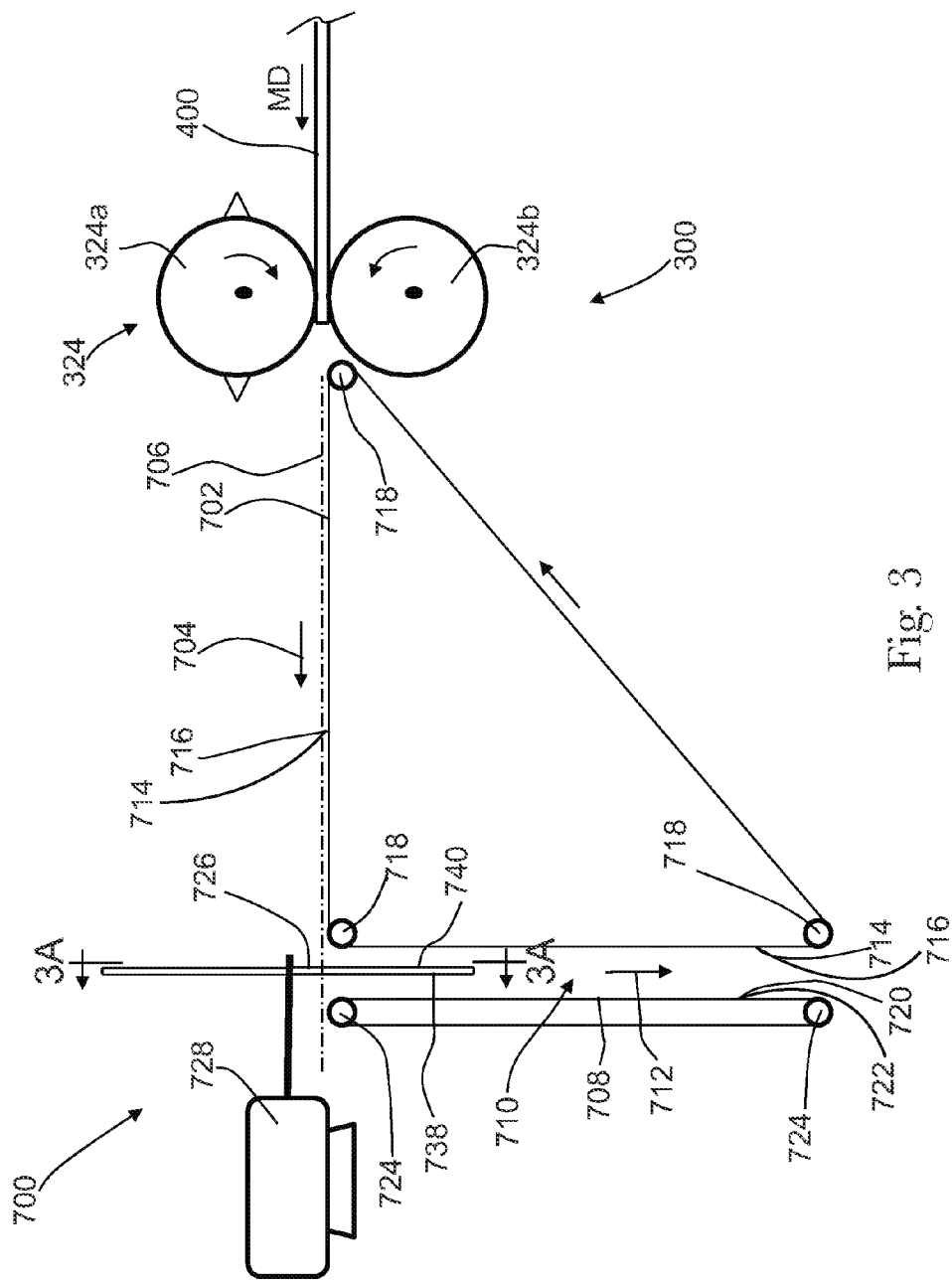
FIG. 3 is a detailed schematic representation of a folding system.
Figure 4:
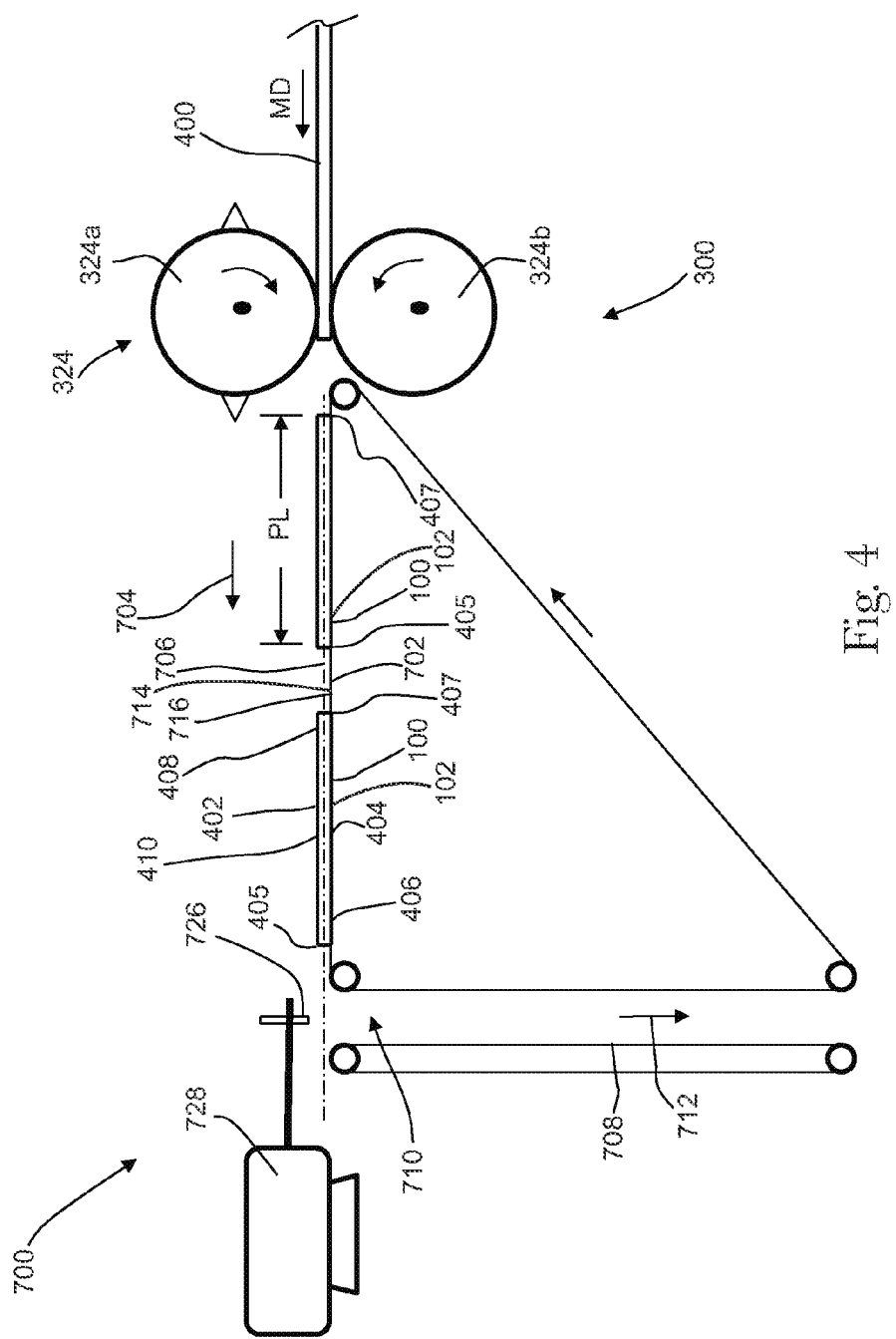
FIG. 4 is a detailed schematic representation the folding system showing absorbent articles advancing in a first direction toward a nip between a first carrier and a second carrier.

As mentioned above, the converting apparatus includes a folding system adapted to fold absorbent articles 100 advancing through the converting process. FIGS. 3-4 show a detailed schematic a downstream portion of a converting apparatus 300 that includes a folding system 700 adapted to fold discrete absorbent articles 100 advancing in a machine direction MD from a final knife 324. The folding system 700 may include a first carrier 702 adjacent the final knife 324, wherein the first carrier 702 advances absorbent articles 100 from the final knife 324 in a first direction 704 to define an article transport plane 706. A second carrier 708 is located adjacent the first carrier 702 to define a nip 710 extending in a second direction 712. More particularly, the first carrier 702 may be in the form of belt conveyor including a first belt 714 defining a first carrier surface 716. As shown in FIG. 3, the first belt 714 may be routed in an endless loop around three rollers 718. The second carrier 708 may be in the form of belt conveyor including a second belt 720 defining a second carrier surface 722. The second belt 720 may be routed in an endless loop around two rollers 724. As such, the nip 710 extends in the second direction between the first carrier surface 716 and the second carrier surface 722. As discussed in more detail below, the first carrier 702 advances discrete absorbent articles 100 in the first direction 704 from the final knife 324. And the first carrier 702 and the second carrier 708 advance folded absorbent articles 100 in the second direction 712 through the nip 710.

With continued reference to FIG. 3, the folding system 700 may also include one or more tucker blades 726 that are rotated adjacent the nip 710. As discussed in more detail below, the tucker blades 726 rotate to engage absorbent articles 100 advancing on the first carrier 702. In turn, the absorbent articles 100 are folded while being forced in the second direction 712 and into the nip 710 by the tucker blades 726.

It is to be appreciated that the folding system 700 may be configured with various numbers of tucker blades 726. For example, as shown in FIG. 3A, the folding system may include a first tucker blade 726a and a second tucker blade 726b. The tucker blades 726a, 726b may be operatively connected with various types of drive mechanisms 728 configured to rotate the tucker blades 726a, 726b around respective axes of rotation 730a, 730b. As shown in FIG. 3A, the first tucker blade 726a is configured to rotate in a direction, A, and the second tucker blade 726b is configured to rotate in an opposite direction, B. In some configurations, the drive mechanisms 728 may include one or more motors directly or indirectly connected with the tucker blades 726a, 726b. In some configurations, a motor may be connected with the tucker blades 726a, 726b through various types of transmission, belt, and/or gear arrangements. In addition, the motors may be configured as servo motors that may operate with constant or variable speeds. Various examples of drive mechanism arrangements that may be used to rotate the tucker blades 726a, 726b are disclosed in U.S. Pat. No. 7,617,656. It is to be appreciated that the drive mechanism 728 may be configured to rotate the tucker blades 726 at a constant angular velocity. In some embodiments, the angular velocity of the tucker blades 726 may be varied on a cyclic basis with a drive mechanism 728 that may include a servo motor.

With continued reference to FIGS. 3 and 3A, each tucker blade includes a first surface 738 and an opposing second surface 740. And each tucker blade 726 includes at least one leading edge 732 and at least one trailing edge 734 connected with each other by an outer circumferential edge 736. As discussed in more detail, during the folding operation, the leading edge 732 and the trailing edge 734 move through the article transport plane 706 as the tucker blade 726 rotates. As shown in FIG. 3A, the tucker blades 726a, 726b are configured to fold two absorbent articles 100 for each complete revolution. Thus, the tucker blades 726a, 726b each include two leading edges 732 and two trailing edges 734. It is to be appreciated that tucker blades 726 can be configured to include more or less than two leading edges 732 and trailing edges 734. It should also be appreciated that embodiments of the folding systems 700 herein may also be configured to fold every other absorbent article 100, thereby providing a method of separating a continuous stream of products into two streams.

It is to be appreciated that the tucker blades may be positioned in various ways with respect to the first and/or second carriers 702, 708. For example as shown FIG. 3A, the axis of rotation 730a of the first tucker blade 726a may be separated in the cross direction CD from the axis of rotation 730b of the second tucker blade 726b. In some configurations, the axes of rotation 730a, 730b may be separated by equal cross directional distances on opposing sides of a machine direction centerline, CL. The machine direction centerline CL may be defined by a longitudinal centerline 114 of an absorbent article 100, 102 advancing in the first direction 704 on the first carrier 702. The axes 730a, 730b may also positioned in various elevations with respect to the first carrier 702. For example, the axes 730a, 730b may be at elevations that are aligned with or offset from the article transport plane 706. As shown in FIG. 3A, the article transport plane 706 is offset in the second direction 712 from a line 742 connecting the axes 730a, 730b.

To provide additional context to the above discussion, the following provides a description of one example implementation of the folding systems and processes herein with respect to FIGS. 3-8.

As shown in FIGS. 3 and 4, a continuous length of absorbent articles 400 advances in a machine direction MD to a final knife 324 that cuts the continuous length of absorbent articles 400 into discrete absorbent articles 100. The final knife 324 may be configured in various ways. For example, the final knife 324 may include a knife roll 324a and an anvil roll 324b. Each discrete absorbent article 100 may be in the form of a diaper 102, such as described above with reference to FIG. 1, and includes a first surface 402 and a second surface 404 opposite the first surface 402. In some configurations, where the absorbent articles 100 are in the form of diapers 102, the first surface 402 may correspond with the inner, body-facing surface 132 and/or topsheet 138, and the second surface 404 may correspond with the outer, garment-facing surface 134 and/or backsheet 140. In other configurations, the first surface 402 may correspond with the outer, garment-facing surface 134 and/or backsheet 140, and the second surface 404 may correspond with the inner, body-facing surface 132 and/or topsheet 138. Each discrete absorbent article 100 also includes a first end 405, a first end region 406, a second end 407, a second end region 408, and a central region 410 intermediate the first and second regions 406, 408. In some configurations, where the absorbent articles 100 are in the form of diapers 102, the first end region 406 may correspond with the first waist region 118; the second end region 408 may correspond with the second waist region 120; and the central region 410 may correspond with the crotch region 122. In addition, the first end 405 may correspond with the first outer edge 128, and the second end 407 may correspond with the second outer edge 130. In other configurations, the first end region 406 may correspond with the second waist region 120, and the second end region 408 may correspond with the first waist region 118. As shown in FIG. 4, the distance between the first end 405 and the second end 407 of the absorbent article 100 along the machine direction MD or first direction 704 defines a pitch length PL.

With continued reference to FIG. 4, the discrete absorbent articles 100 advance to the first carrier 702 from the final knife 324. The absorbent articles 100 are oriented such that the second surface 404 is in a facing relationship with and in contact with the first carrier surface 716. The first carrier 702 advances the absorbent articles 100 in the first direction 704 such that the first end 405 of each absorbent article 100 is a leading end and the second end 407 is a trailing end. It is to be appreciated that the first direction 704 may correspond with the machine direction MD. The continuous length of absorbent articles 400 may advance to the final knife 324 at a first speed, S1. And the first carrier 702 may advance the discrete absorbent articles 100 from the final knife 324 at a second speed, S2. In some configurations, the second speed S2 may be the same as the first speed S1. In other configurations, the second speed S2 may be greater than the first speed S1. And as such, the first carrier 702 may accelerate the discrete absorbent articles 100 advancing from the final knife 324 to the second speed S2, which in turn, causes consecutive absorbent articles 100 on the first carrier 702 to be spaced apart from each other along the first direction 704. As shown in FIG. 4, the advancement of the discrete absorbent articles 100 in the first direction 704 on the first carrier 702 defines an article transport plane 706 along which the absorbent articles 100 are transported.

Figure 5:
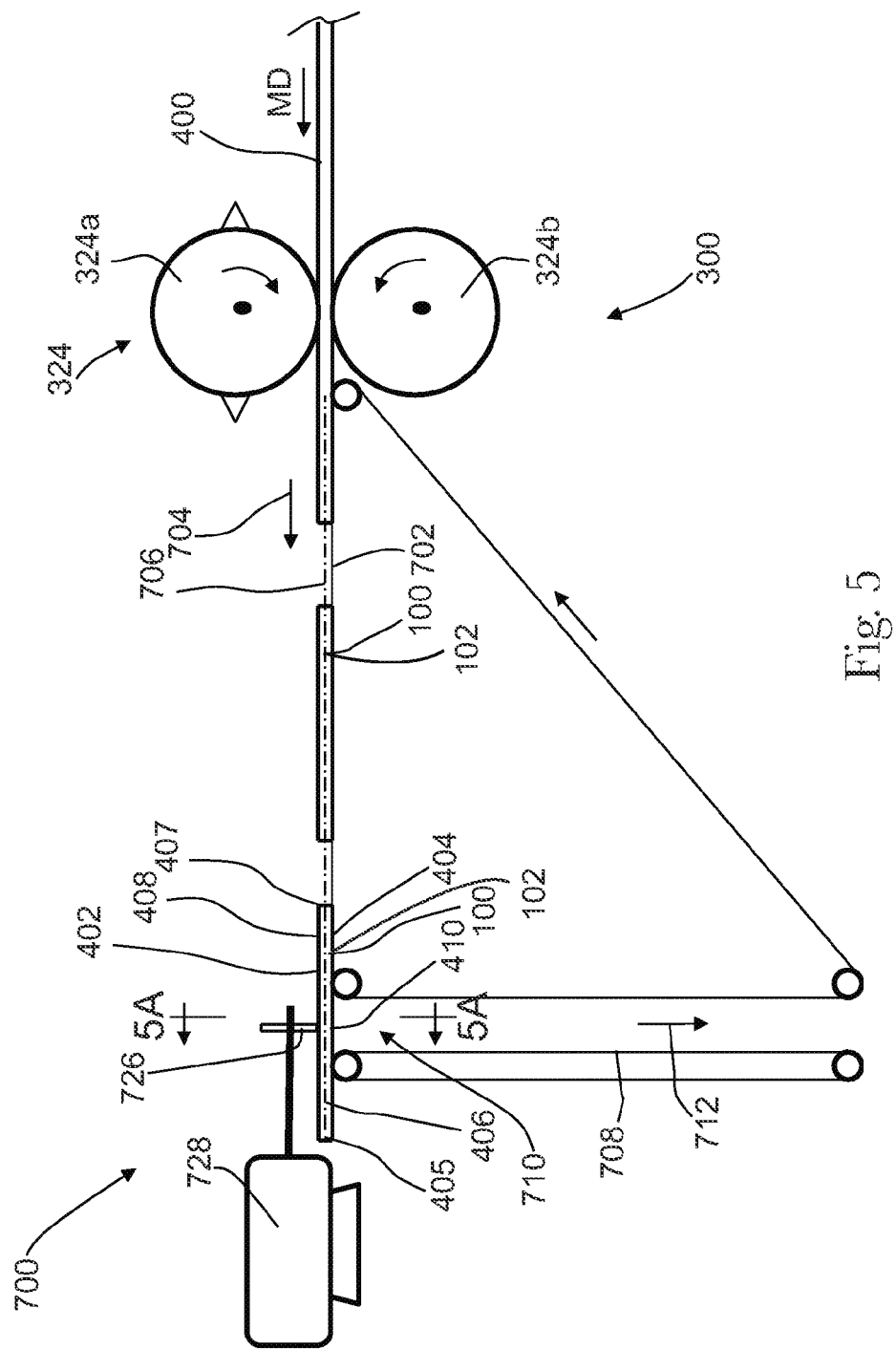
FIG. 5 is a detailed schematic representation the folding system showing an absorbent article with a first end and first end region advanced past the nip.
Figure 5A:
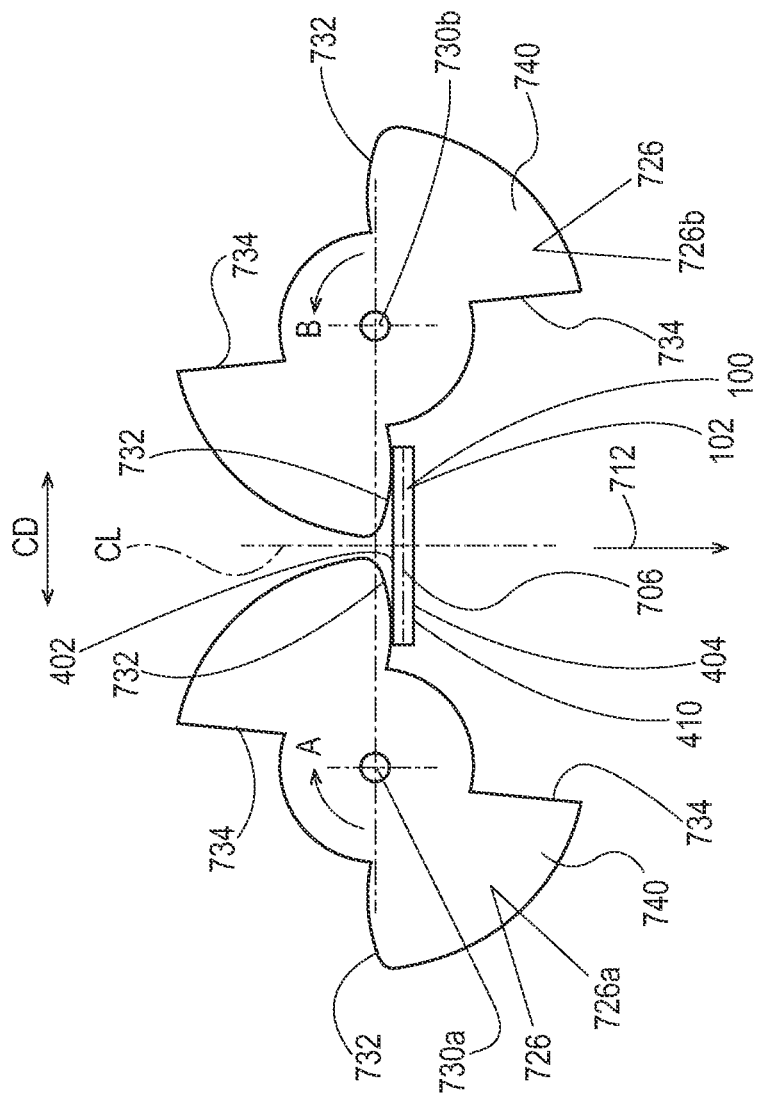
FIG. 5A is a view of two tucker blades from FIG. 5 taken along line 5A-5A.
Figure 6:
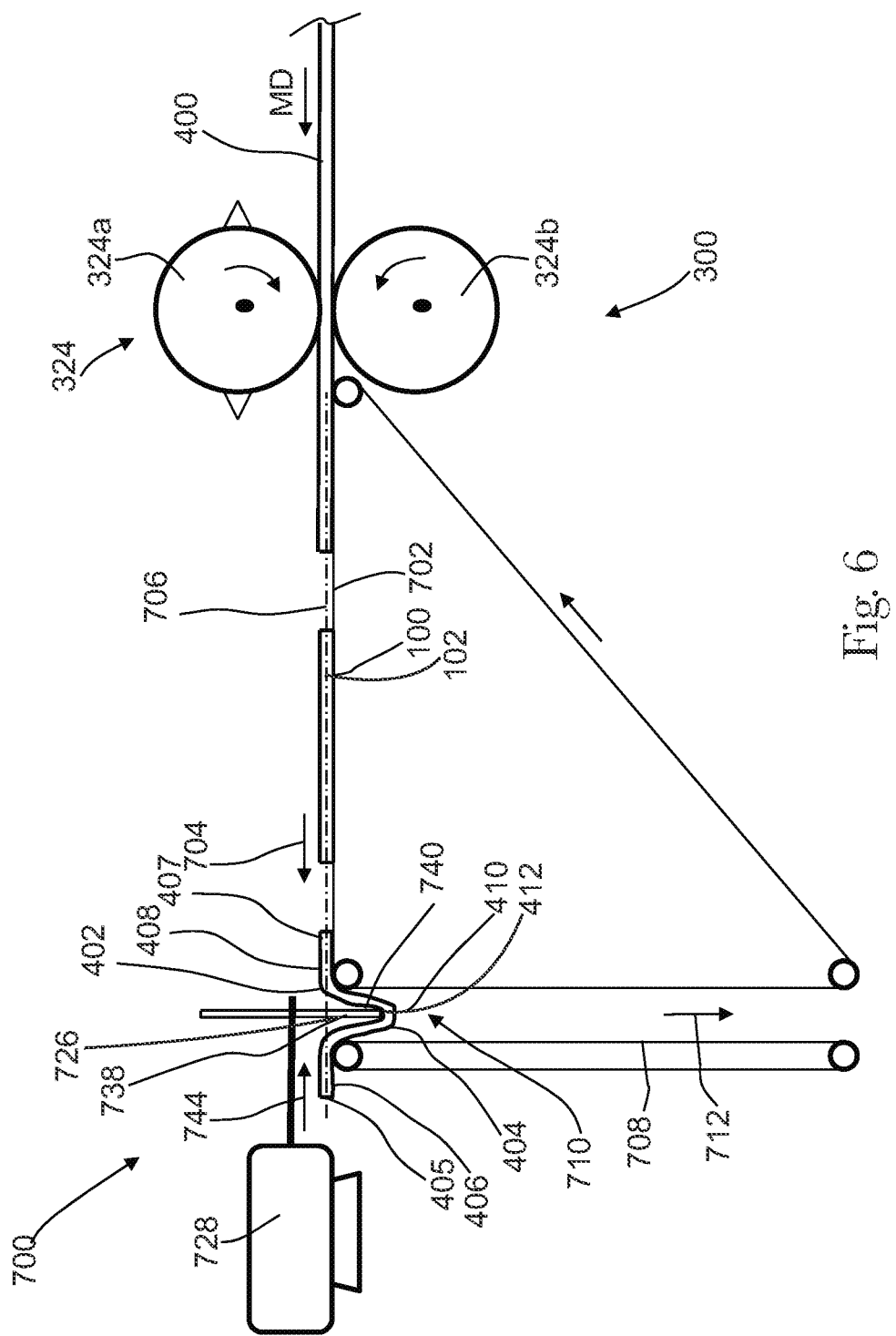
FIG. 6 is a detailed schematic representation the folding system showing the tucker blades redirecting a central region of the absorbent article in a second direction into the nip.

As shown in FIGS. 4 and 5, the first carrier 702 conveys each discrete absorbent article 100 along the article transport plane 706 such that the first end 405 and the first end region 406 of each absorbent article 100 advances in the first direction 704 past the nip 710 and the rotating tucker blades 726. With reference to FIGS. 5 and 5A, the tucker blades 726a, 726b are rotated such that leading edges 732 of the tucker blades 726a, 726b contact the first surface 402 of the absorbent article 100 in the central region 410, thereby creating a fold line 412 extending in a cross direction CD across the central region 410 of the absorbent article 100. Referring now to FIG. 6, as the tucker blades 726a, 726b continue to rotate, the leading edges 732 move through the article transport plane 706 and redirect the central region 410 of the absorbent article 100 in the second direction 712 and into the nip 710. It is to be appreciated that the folding system 700 may be configured such that the leading edges 732 of the tucker blades 726 contact the absorbent articles 100 so as create fold lines 412 that are equidistant from the first end 405 and the second end 407. As such, in some configurations, the fold lines 412 may be positioned so as to bisect the article 100. It is also to be appreciated that the folding systems and methods herein may be configured to bi-fold, tri-fold, and/or quad-fold various types of absorbent articles 100. As such, the fold line 412 may be positioned in various locations other than the geometric center of the absorbent articles 100.

Figure 7:
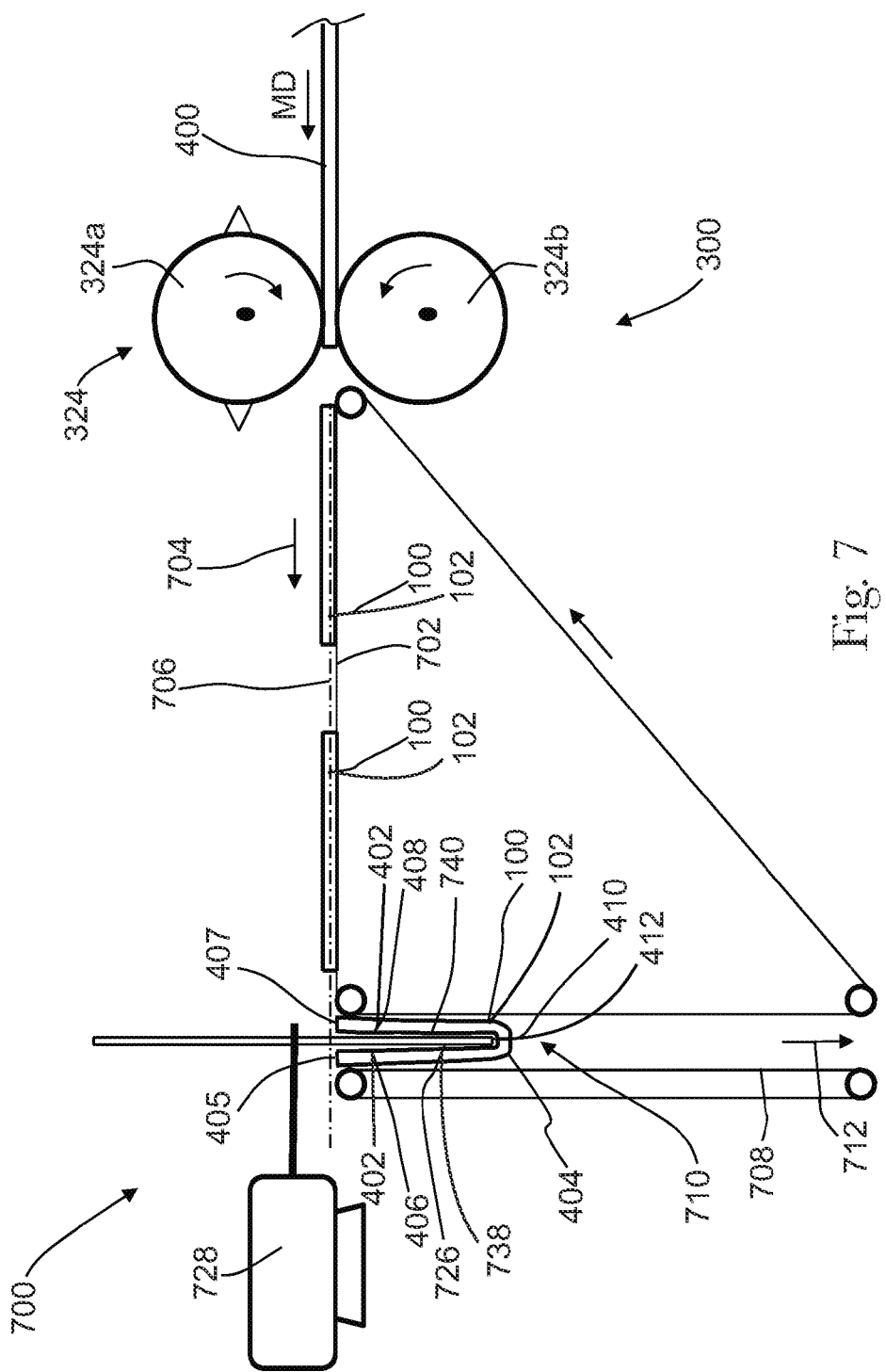
FIG. 7 is a detailed schematic representation the folding system showing opposing end regions of a folded absorbent article contacting opposing sides of the tucker blades.

With continued reference to FIG. 6, as the central region 410 of the absorbent article is redirected into the nip 710 by the tucker blades 726a, 726b, the second end 407 of the absorbent article 100 continues to move in the first direction 704 toward the second surface 740 of the tucker blades 726. At the same time, movement of the first end 405 of the absorbent article 100 reverses and moves in a third direction 744 toward the first surfaces 738 of the tucker blades 726. Referring now to FIG. 7, the leading edges 732 of the tucker blades 726 continue to push the absorbent article 100 along the fold line 412 in the second direction 712 through the nip 710, the first surface 402 of the first end region 406 of the absorbent article 100 is brought into a facing relationship with the first surface 738 of the tucker blades 726. At the same time, the first surface 402 of the second end region 408 of the absorbent article 100 is brought into a facing relationship with the second surface 740 of the tucker blades 726. And when the absorbent article 100 is completely folded, the first end 405 and the second end 407 of the absorbent article 100 are separated by first and second surfaces 738, 740 of the tucker blades 726. Thus, instead of colliding with each other during the folding process, the first and second end regions 406, 408, and first and second ends 405, 407, of the absorbent article 100 are brought into contact with opposing sides 738, 740 of the tucker blades 726.

Figure 8:
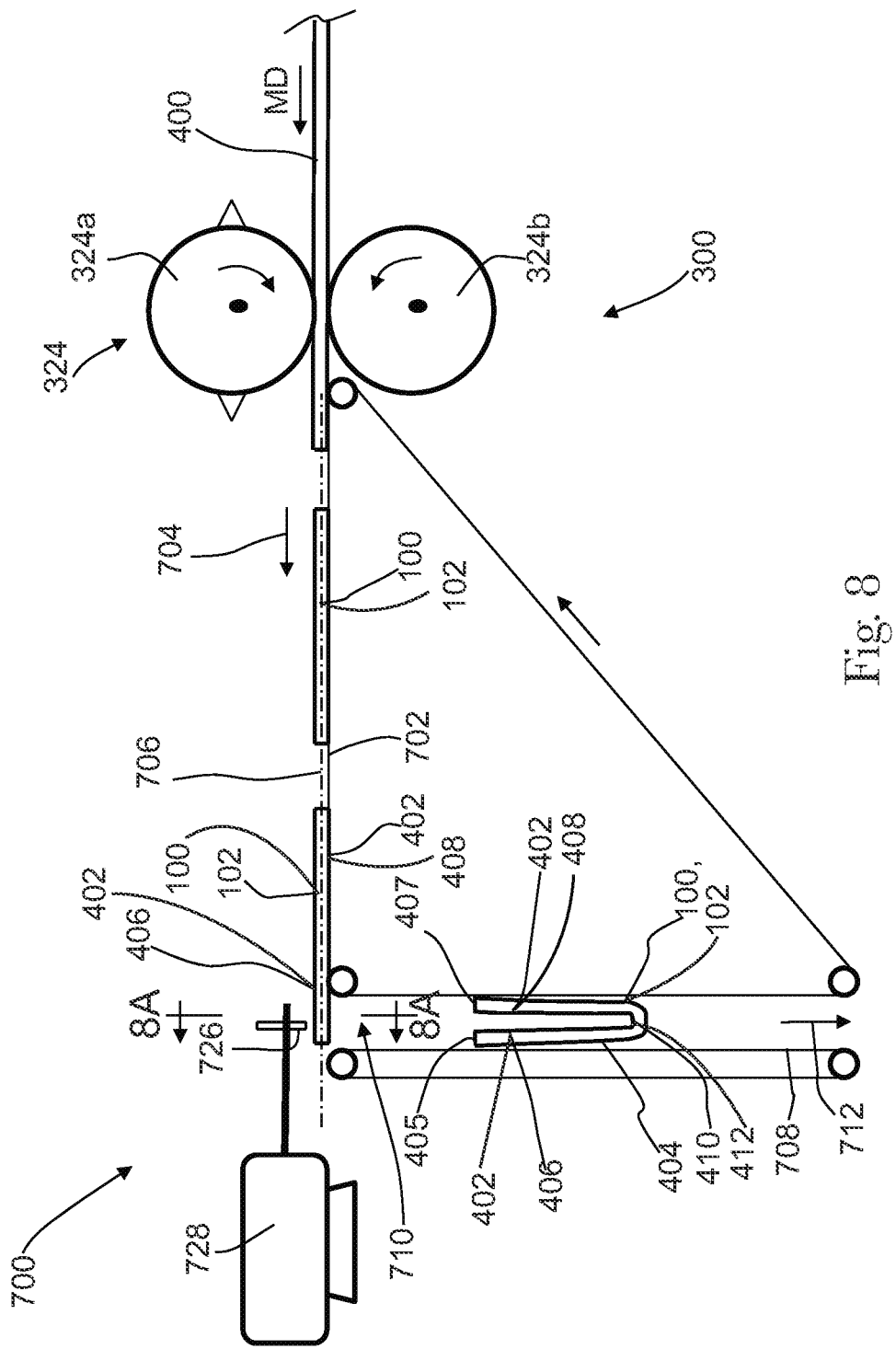
FIG. 8 is a detailed schematic representation the folding system showing the folded absorbent article advancing in the second direction through the nip.
Figure 8A:
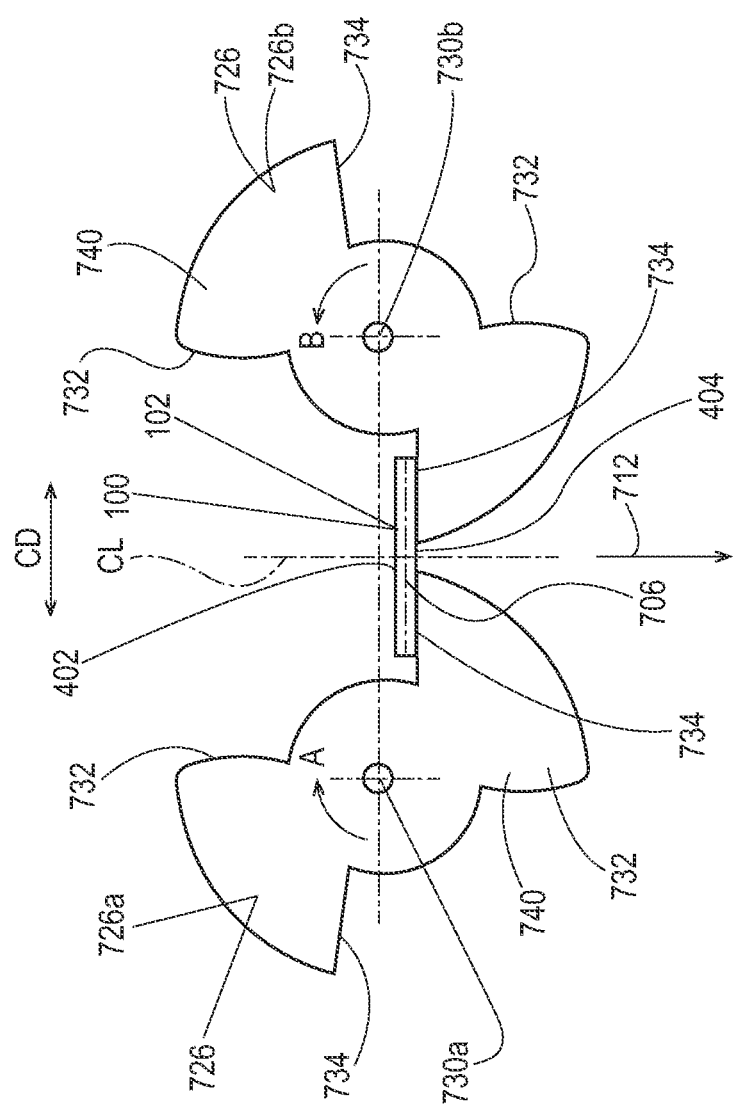
FIG. 8A is a view of two tucker blades from FIG. 8 taken along line 8A-8A.

As shown in FIG. 8, the folded absorbent articles 100 are conveyed in the second direction 712 through the nip 712 between the first carrier 702 and the second carrier 708 and away from the article transport plane 706 and from the tucker blades 726. And the tucker blades 726 continue to rotate as a subsequently advancing absorbent article 100 is conveyed in the first direction 704 by the first carrier 702 toward the nip 710 and tucker blades 726. As shown in FIGS. 8 and 8A, the tucker blades 726 continue to rotate such that the trailing edges 734 move through the article transport plane 706 far enough to allow first end region 406 of the subsequently advancing absorbent article 100 to advance past the nip 710 without colliding with the second surface 740 of the tucker blades 726. As shown in FIG. 8A, the trailing edges 734 of the tucker blades 726 may also be configured with straight edges that are oriented to be parallel with the article transport plane 706 at least once during a complete rotation of the tucker blades as a subsequently advancing absorbent article 100 to advances toward the nip 710.

FIG. 3A shows a detailed view of a tucker blade 726a showing how the relative positions of a leading edge 732 and a trailing edge 734 may be defined by a sweep angle, $\theta$, between a first radial line 746 and a second radial line 748. The first radial line 746 extends from the axis of rotation 730a to a portion of the leading edge 732 that first crosses the article transport plane 706 during rotation of the tucker blade 732. And the second radial line 748 extends from the axis of rotation 730a to a portion of the trailing edge 734 that last crosses the article transport plane 706 during rotation of the tucker blade 732.

As previously mentioned, embodiments of the tucker blades 726 discussed herein may be configured with a sweep angle, $\theta$, wherein a leading edge 732 is positioned relative to a trailing edge 734 such that the first and the second end regions 406, 408 of the absorbent articles 100 do not collide with each other during the folding process. In some embodiments, when folding diapers 102, the tucker blades 726 discussed may be configured with a sweep angle, $\theta$, such that the trailing edge 734 of the tucker blade 726 separates the body-facing surface 132 of the first waist region 118 from the body-facing surface 132 of the second waist region 120, from fold line 412 at least a longitudinal edge of one or more previously folded ears 104, 106, 108, 110. In addition, embodiments of the tucker blades 726 discussed herein may be configured with a sweep angle, $\theta$, such that the trailing edge 734 is positioned relative to the leading edge 732 so that after an absorbent article has been folded, a subsequently advancing absorbent article does not collide with the tucker blades 726 while moving toward the nip 712. In some embodiments, a length of an arcuate sector extending from the leading edge 732 of the tucker blade 736 to the trailing edge 734 of the tucker blade 726 may be substantially equal to a distance from fold line 412 to either or both the first end 405 and/or the second end 507 in a radial region of these leading and trailing edges 732, 734 that contact the absorbent article 100 during the folding process.

In some embodiments, taking into account various operating parameters of the folding system 700, the tucker blade 726a may be configured with the sweep angle, $\theta$, such that opposing end regions of absorbent articles do not collide with each other while being folded, while also allowing subsequently advancing absorbent articles avoid colliding with the tucker blade 726a. In such an example and in the context of the discussion above when a fold line 412 is intended to bisect the pitch length PL, the sweep angle, $\theta$ (degrees), may be defined by the following equation:

$$\theta = (0.18*PL*S1)/(S2*n),$$

wherein PL is the pitch length (mm) of the absorbent article; S1 is the speed (articles/minute) at which the continuous length of absorbent articles 400 may advance to the final knife 324; S2 is speed (meters/minute) at which the first carrier 702 may advance the discrete absorbent articles 100 from the final knife 324; and n is the number of discrete absorbent articles 100 folded by the tucker blade 726 during one full revolution of the tucker blade 726. In some configurations, (PL/1000)*S1 is less than S2. And in some configurations, (PL/1000)*S1 is equal to S2.

In another example and in the context of the discussion above taking into account the intended position of the fold line 412 on the absorbent article 100, the sweep angle, $\theta$ (degrees), may be defined by the following equation:

$$\theta = (1-POS)*(0.36*PL*S1)/(S2*n),$$

wherein PL is the pitch length (mm) of the absorbent article; S1 is the speed (articles/minute) at which the continuous length of absorbent articles 400 may advance to the final knife 324; S2 is speed (meters/minute) at which the first carrier 702 may advance the discrete absorbent articles 100 from the final knife 324; n is the number of discrete absorbent articles 100 folded by the tucker blade 726 during one full revolution of the tucker blade 726; and wherein POS is calculated as the ratio of the distance of between the fold line 412 and a first end (or leading end) 405 to the pitch length PL. For example, when the fold line 412 is intended to bisect the absorbent article, POS may be 0.5. In another example, such as when the fold line 412 is intend to be positioned from the first end 405 by a distance of ⅓ of the pitch length PL, POS may be 0.33.

Although the present disclosure is provided in the context of manufacturing absorbent articles, and diapers in particular, it is to be appreciated that the systems and methods disclosed herein may be applied to the manufacture of various types of articles and products involving the monitoring of various different types of substrates and/or components. Examples of other products include absorbent articles for inanimate surfaces such as consumer products whose primary function is to absorb and retain soils and wastes that may be solid or liquid and which are removed from inanimate surfaces such as floors, objects, furniture and the like. Non-limiting examples of absorbent articles for inanimate surfaces include dusting sheets, pre-moistened wipes or pads, paper towels, dryer sheets. Additional examples of products include absorbent articles for animate surfaces whose primary function is to absorb and contain body exudates and, more specifically, devices which are placed against or in proximity to the body of the user to absorb and contain the various exudates discharged from the body. Non-limiting examples of incontinent absorbent articles include diapers, adult incontinence briefs and undergarments, feminine hygiene garments such as panty liners, absorbent inserts, and the like, toilet paper, tissue paper, facial wipes or cloths, toilet training wipes. Still other examples of products include packaging components and substrates and/or containers for laundry detergent, which may be produced in pellets or pouches and may be manufactured in a converting or web process or even discreet products produced at high speed such as high-speed bottling lines or cosmetics. Still other examples of products include a web substrate containing labels to be placed on bottles and/or containers for laundry detergent, fabric enhancers, hair and beauty care products, and cleaning products. Further, it is to be appreciated that although the present disclosure often refers to monitoring or viewing substrates and/or webs, it is to be appreciated that the inspection systems discussed herein can be used to monitor and/or view combinations of webs and individual components as well as parts added as a continuous web of material and parts added as a discontinuous web of material.

It is also to be appreciated that various components of the converting apparatus 300 may have various configurations. For example, although the first carrier 702 and the second carrier 708 are depicted as belt conveyors, it is to be appreciated that the first carrier 702 and/or the second carrier 708 may be configured in various ways. For example, in some embodiments, the first carrier 702 and/or second carrier 708 may be configured as a rotating drum. In order to help mitigate problems associated with uncontrolled movement of the discrete diapers 100 during conveyance, the first carrier 702 and/or second carrier 708 may also include a vacuum system in communication with a porous and/or apertured belt or other foraminous carrier surface 716, 722 that allows the suction force of the vacuum system to be exerted on absorbent articles 100. In some embodiments, additional belt conveyors may be located adjacent the first and/or second carriers 702, 708 to create additional nips extending along the first direction 704, wherein absorbent articles 100 are maintained in a flattened state while advancing in the first direction 704.

As discussed above with reference to FIG. 6, as the central region 410 of the absorbent article is redirected into the nip 710 by the tucker blades 726, the second end 407 of the absorbent article 100 continues to move in the first direction, while movement of the first end 405 of the absorbent article 100 reverses and moves in a third direction 744 toward the tucker blades 726. As such, the sudden reversal and change of direction in movement during the folding process subjects the first end 405 and first end region 406 of the article 100 to snapback and whipping effects that may result in damage to the article and/or displacement of components thereof. For example, when folding diapers, excessive g-forces resulting from theses snapback and/or whipping effects may cause wrinkled and/or displaced ears in the folded diapers and sometimes may cause damage to absorbent core. Thus, embodiments of the folding system 700 such as shown in FIG. 9 may include one or more guides 750 adjacent the nip 710 to help reduce the aforementioned snapback and whipping effects.

As shown in FIG. 9, the folding system 700 includes a first guide plate 750a and a second guide plate 750b positioned downstream of the nip 710. The first guide plate 750a is also separated from the second plate 750b by opposing sides of the article transport plane 706. The guide plates 750 may be angled toward each other or may be parallel, and may be curved or straight. For example in FIG. 9, the guide plates 750 may converge along the first direction 704. As shown in FIG. 9, during the folding process he first end 405 and first end region 406 of the article 100 advances in the first direction 706 past the nip 710 and in between the first guide plate 750a and the second guide plate 750b. More particularly, the first surface 402 of the first end region 406 is in a facing relationship with the first guide plate 750a, and the second surface 404 of the first end region 406 is in a facing relationship with the second guide plate 750b. As the central region 410 of the absorbent article is redirected into the nip 710 by the tucker blades 726, the first and second guide plates 750a, 750b help constrain movement of the first end region 406 relative to the article transport plane 706 while movement of the first end 405 of the absorbent article 100 reverses and moves in the third direction 744 toward the tucker blades 726.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for folding absorbent articles, the method comprising the steps of:
    conveying an absorbent article in a first direction on a first carrier to define an article transport plane, wherein the absorbent article includes a first surface and a second surface opposite the first surface, wherein the absorbent article includes a first end and a second end, and wherein the absorbent article includes a first end region and a second end region, and a central region located between the first and second end regions;

advancing the first end and the first end region past a nip defined between the first carrier and a second carrier;

rotating a tucker blade, wherein the tucker blade includes a first surface and a second surface opposite the first surface, and wherein the tucker blade includes a leading edge and a trailing edge, wherein the leading edge and the trailing edge move through the article transport plane at the nip as the tucker blade rotates;

folding the absorbent article by redirecting the central region of the absorbent article in a second direction into the nip with the leading edge of the tucker blade thereby creating a fold line across the central region of the absorbent article, positioning the first surface of the absorbent article extending from the fold line to the first end into contact with the first surface of the tucker blade and positioning the first surface of the absorbent article extending from the fold line to the second end into contact with the second surface of the tucker blade, wherein the first end and the second end of the absorbent article are separated by the tucker blade; and conveying the folded absorbent article in the second direction between the first carrier and the second carrier away from the article transport plane.

2. The method of claim 1, further comprising the step of: advancing a continuous length of absorbent articles at a first speed, S1, in a machine direction.

3. The method of claim 2, further comprising the step of: cutting the absorbent article from the continuous length of absorbent articles, wherein the absorbent article includes a pitch length, PL, defined by a distance in the machine direction between the first end and the second end.

4. The method of claim 3, wherein the absorbent article is conveyed at a second speed, S2, on the first carrier.

5. The method of claim 4, further comprising the step of folding, n, discrete absorbent articles with one full revolution of the tucker blade.

6. The method of claim 5, wherein a sweep angle, θ, between the leading edge and the trailing edge of the tucker blade is calculated as (0.18*PL*S1)/(S2*n), wherein the sweep angle, θ is expressed in units of (degrees); PL is expressed in units of (mm), S1 is expressed in units of (articles/minute), S2 is expressed in units of (meters/minute); and n is expressed in units of (articles).

7. The method of claim 6, wherein (PL/1000)*S1 is less than S2, wherein (PL/1000)*S1 is expressed in units of (meters/minute).

8. The method of claim 6, wherein (PL/1000)*S1 is equal to S2, wherein (PL/1000)*S1 is expressed in units of (meters/minute).

9. The method of claim 1, wherein the first carrier comprises a belt conveyor.

10. The method of claim 1, wherein the second carrier comprises a belt conveyor.

11. The method of claim 1, wherein the absorbent article comprises a diaper, and wherein the first end region comprises a front waist region, and wherein the second end region comprises a rear waist region.

12. The method of claim 1, wherein the first surface of the absorbent article comprises a wearer facing surface.

13. A method for folding absorbent articles, the method comprising the steps of:

advancing a continuous length of absorbent articles at a first speed, S1, in a machine direction;

cutting the continuous length of absorbent articles into discrete absorbent articles, wherein each discrete absorbent article includes a first surface and a second surface opposite the first surface, wherein each discrete absorbent article includes a first end region and a second end region, and a central region located between the first and second end regions, and wherein each discrete absorbent article includes a first end and a second end, and a having a pitch length, PL, defined by a distance in the machine direction between the first end and the second end;

conveying each discrete absorbent articles at a second speed S2, in a first direction on a first carrier to define an article transport plane;

advancing the first end and the first end region of each discrete absorbent article past a nip defined between the first carrier and a second carrier;

rotating a tucker blade, wherein the tucker blade includes a first surface and a second surface opposite the first surface, and wherein the tucker blade includes a leading edge and a trailing edge, wherein the leading edge and the trailing edge move through the article transport plane at the nip as the tucker blade rotates;

folding n discrete absorbent articles with one full revolution of the tucker blade by redirecting the central region of each discrete absorbent article in a second direction into the nip with the leading edge thereby creating a fold line across the central region of each discrete absorbent article, positioning the first surface of each discrete absorbent article extending from the fold line to the first end the first end into contact with the first surface of the tucker blade and positioning the first surface of each discrete absorbent article extending from the fold line to the second end the contact with the second surface of the tucker blade, and wherein a sweep angle, between the leading edge and the trailing edge of the tucker blade is calculated as (0.18*PL*S1)/(S2*n); and wherein the sweep angle, is expressed in units of (degrees); PL is expressed in units of (mm), S1 is expressed in units of (articles/minute), S2 is expressed in units of (meters/minute); and n is expressed in units of (articles).

14. The method of claim 13, further comprising the step of conveying the folded absorbent article in the second direction between the first carrier and the second carrier away from the article transport plane.

15. The method of claim 13, wherein the first carrier comprises a belt conveyor.

16. The method of claim 13, wherein the second carrier comprises a belt conveyor.

17. The method of claim 13, wherein the absorbent article comprises a diaper, and wherein the first end region comprises a front waist region, and wherein the second end region comprises a rear waist region.

18. The method of claim 13, wherein the first surface of the absorbent article comprises a wearer facing surface.

* * * * *